US006931361B2

(12) United States Patent
Opsal et al.

(10) Patent No.: US 6,931,361 B2
(45) Date of Patent: Aug. 16, 2005

(54) REAL TIME ANALYSIS OF PERIODIC STRUCTURES ON SEMICONDUCTORS

(75) Inventors: Jon Opsal, Livermore, CA (US); Hanyou Chu, San Jose, CA (US)

(73) Assignee: Therma-Wave, Inc., Fremont, CA (US)

( * ) Notice: Subject to any disclaimer, the term of this patent is extended or adjusted under 35 U.S.C. 154(b) by 0 days.

(21) Appl. No.: 10/877,397

(22) Filed: Jun. 25, 2004

(65) Prior Publication Data

US 2004/0233462 A1 Nov. 25, 2004

Related U.S. Application Data

(60) Continuation of application No. 10/405,541, filed on Apr. 2, 2003, now Pat. No. 6,778,911, which is a division of application No. 09/906,290, filed on Jul. 16, 2001, now Pat. No. 6,704,661.

(51) Int. Cl.[7] .............................................. G06F 17/00
(52) U.S. Cl. ........................ 702/189; 702/159; 702/172; 356/625
(58) Field of Search ............................. 702/189, 27, 28, 702/22, 40, 66, 70–73, 76, 127, 159, 166, 172, 183, 167, 170, 155, 35; 356/369, 908, 937, 947, 237.4, 237.5, 625, 636, 445, 446, 448, 634, 635, 451, 630, 632, 300–303, 511, 512, 601, 388, 392–394; 703/1, 2, 4, 7, 12; 382/145; 250/559.2, 559.24, 559.39; 438/7, 14, 16; 700/119, 120

(56) References Cited

U.S. PATENT DOCUMENTS

| 4,999,014 | A |   | 3/1991 | Gold et al. ................. 356/382 |
| 5,042,951 | A |   | 8/1991 | Gold et al. ................. 356/369 |
| 5,181,080 | A |   | 1/1993 | Fanton et al. ............... 356/381 |
| 5,412,473 | A |   | 5/1995 | Rosencwaig et al. ....... 356/351 |
| 5,596,411 | A |   | 1/1997 | Fanton et al. ............... 356/369 |
| 5,607,800 | A |   | 3/1997 | Ziger ............................. 430/8 |
| 5,608,526 | A |   | 3/1997 | Piwonka-Corle et al. ... 356/369 |
| 5,739,909 | A |   | 4/1998 | Blayo et al. ................ 356/369 |
| 5,864,633 | A |   | 1/1999 | Opsal et al. ................ 382/141 |
| 5,867,276 | A |   | 2/1999 | McNeil et al. .............. 356/445 |
| 5,889,593 | A |   | 3/1999 | Bareket ....................... 356/445 |
| 5,963,329 | A |   | 10/1999 | Conrad et al. .............. 356/372 |
| 6,100,985 | A | * | 8/2000 | Scheiner et al. ............ 356/630 |

(Continued)

FOREIGN PATENT DOCUMENTS

| WO | WO 99/02970 | 1/1999 | .......... G01N/21/21 |
| WO | WO 99/45340 | 9/1999 | .......... G01B/11/02 |
| WO | PCT/US01/27552 | 9/2001 | .......... G02B/5/00 |
| WO | WO 02 23231 A2 | 3/2002 | .......... G02B/5/00 |

OTHER PUBLICATIONS

U.S. Appl. No. 09/818,703, filed Mar. 27, 2001, entitled "Critical Dimension Analysis with Simultaneous Multiple Angle of Incidence Measurements," by Jon Opsal et al., 26 pages of specification and 2 sheets of informal drawings.

*Primary Examiner*—Hal Wachsman
(74) *Attorney, Agent, or Firm*—Stallman & Pollock LLP

(57) ABSTRACT

A system for characterizing periodic structures formed on a sample on a real time basis is disclosed. A spectroscopic measurement module generates output signals as a function of wavelength. The output signals are supplied to a processor for evaluation, which creates an initial theoretical model having a rectangular structure. The processor calculates the theoretical optical response of that sample, which is compared to normalized measured values at each of a plurality of wavelengths. The model configuration is then modified to be closer to the actual measured structure. The processor recalculates the optical response and compares the result to the normalized data. This process is repeated in an iterative manner until a best fit rectangular shape is obtained. Thereafter, the complexity of the model is iteratively increased, and model is iteratively fit to the data until a best fit model is obtained which is similar to the periodic structure.

10 Claims, 3 Drawing Sheets

U.S. PATENT DOCUMENTS

| | | | |
|---|---|---|---|
| 6,281,974 B1 | 8/2001 | Scheiner et al. | 356/381 |
| 6,429,943 B1 | 8/2002 | Opsal et al. | 356/625 |
| 6,465,265 B2 | 10/2002 | Opsal et al. | 438/16 |
| 6,483,580 B1 * | 11/2002 | Xu et al. | 356/300 |
| 6,556,947 B1 | 4/2003 | Scheiner et al. | 702/172 |
| 6,657,736 B1 * | 12/2003 | Finarov et al. | 356/625 |
| 6,694,284 B1 * | 2/2004 | Nikoonahad et al. | 702/155 |
| 2002/0035455 A1 | 3/2002 | Niu et al. | 703/4 |

* cited by examiner

REAL TIME ANALYSIS OF PERIODIC STRUCTURES ON SEMICONDUCTORS

CLAIM OF PRIORITY

This application is a continuation of U.S. application Ser. No. 10/405,541, filed Apr. 2, 2003, now U.S. Pat. No. 6,778,911, which is a divisional of U.S. application Ser. No. 99/906,290, filed Jul. 16, 2001, now U.S. Pat. No. 6,704,661.

TECHNICAL FIELD

The subject invention relates to the analysis of data obtained during the measurement of periodic structures on semiconductors. In particular, an approach is disclosed which allows accurate, real time analysis of such structures.

BACKGROUND

The semiconductor industry is continually reducing the size of features on wafers. These features include raised profiles and trenches that have a particular height (or depth), width and shape (contour). Accurate measurement of these features is necessary to insure appropriate yields.

Technologies suitable for measuring these small periodic features (critical dimensions) are quite limited. Optical measurement technology is the most desirable since it is a non-contact technique. However, the smallest spot size of conventional optical probe beams is larger than the size of the periodic features which need to be measured.

FIG. 1 illustrates a substrate 8 having basic periodic pattern 10 formed thereon. The pattern will have a certain characteristic height (H), separation (S) and width (W). Note that in this illustration, the side walls of the structure are not vertical, so the width varies over the height of the structure. FIG. 1 also schematically indicates a probe beam spot 12 which is larger than the spacing between the individual features.

The difficulty in directly measuring such small structures has lead to the development of scatterometry techniques. These techniques have in common the fact that light reflected from the periodic structure is scattered and can be treated mathematically as light scattered from a grating. A significant effort has been made to develop metrology devices that measure and analyze light scattered from a sample in order to evaluate the periodic structure.

For example, U.S. Pat. No. 5,607,800 discloses the concept of measuring reflected (scattered) light created when a broad band probe beam interacts with a sample. The reflected light intensity as a function of wavelength is recorded for a number of reference samples having known periodic features. A test sample is then measured in a similar manner and the output is compared to the output obtained from the reference samples. The reference sample which had the closest match in optical response to the test sample would be assumed to have a periodic structure similar to the test sample.

A related approach is disclosed in U.S. Pat. No. 5,739,909. In this system, measurements from a spectroscopic ellipsometer are used to characterize periodic structures. In this approach, the change in polarization state as a function of wavelength is recorded to derive information about the periodic structure.

Additional background is disclosed in U.S. Pat. No. 5,867,276. This patent describes some early efforts which included measuring the change in intensity of a probe beam as a function of angle of incidence. Measurements at multiple angles of incidence provide a plurality of separate data points. Multiple data points are necessary to evaluate a periodic structure using a fitting algorithm. In the past, systems which took measurements at multiple angles of incidence required moving the sample or optics to vary the angle of incidence of the probe beam. More recently, the assignee herein developed an approach for obtaining scatterometry measurements at multiple angles of incidence without moving the sample or the optics. This approach is described in U.S. patent application Ser. No. 09/818,703, filed Mar. 27, 2001 now U.S. Pat. No. 6,429,943.

U.S. Pat. No. 5,867,276, like the other prior art discussed above, addresses the need to obtain multiple data points by taking measurements at multiple wavelengths. This patent is also of interest with respect to its discussion of analytical approaches to determining characteristics of the periodic structure based on the multiple wavelength measurements. In general, these approaches start with a theoretical model of a periodic structure having certain attributes, including width, height and profile. Using Maxwell's equations, the response which a theoretical structure would exhibit to incident broadband light is calculated. A rigorous coupled wave theory can be used for this analysis. The results of this calculation are then compared to the measured data (actually, the normalized data). To the extent the results do not match, the theoretical model is modified and the theoretical data is calculated once again and compared to the measured data. This process is repeated iteratively until the correspondence between the calculated data and the measured data reaches an acceptable level of fitness. At this point, the characteristics of the theoretical model and the actual sample should be very similar.

The calculations discussed above are relatively complex even for the most simple models. As the models become more complex (particularly as the profiles of the walls of the features become more complex) the calculations become exceedingly long and complex. Even with today's high speed processors, the art has not developed a suitable approach for analyzing more complex structures to a highly detailed level on a real time basis. Analysis on a real time basis is very desirable so that manufacturers can immediately determine when a process is not operating correctly. The need is becoming more acute as the industry moves towards integrated metrology solutions wherein the metrology hardware is integrated directly with the process hardware.

One approach which allows a manufacturer to characterize features in real time is to create "libraries" of intensity versus wavelength plots associated with a large number of theoretical structures. This type of approach is discussed in PCT application WO 99/45340, published Sep. 10, 1999 as well as the references cited therein. In this approach, a number of possible theoretical models are created in advance of the measurement by varying the characteristics of the periodic structure. The expected optical response is calculated for each of these different structures and stored in a memory to define a library of solutions. When the test data is obtained, it is compared to the library of stored solutions to determine the best fit.

While the use of libraries does permit a relatively quick analysis to be made after the sample has been measured, it is not entirely satisfactory for a number of reasons. For example, each time a new recipe is used (which can result from any change in structure, materials or process parameters), an entirely new library must be created. Further, each library generated is unique to the metrology tool used to make the measurements. If the metrology tool is altered in any way (i.e., by replacing an optical element that alters the measurement properties of the tool), a new library must be created. In addition, the accuracy of the results is limited by the number of models stored in the library. The more models that are stored, the more accurate the result, however, the longer it will take to create the library and the longer it will take to make the comparison. The most ideal solution would be to develop a system which permitted iterative (fitting) calculations to be performed in real time and which is easily modified to account for changes in the metrology tool and the process begin monitored.

One approach to speeding up the fitting calculation can be found in U.S. Pat. No. 5,867,276. (The latter patent and the other publications cited above are all incorporated herein by reference.) This patent discloses a method of reducing the number of parameters needed to characterize the shape or profile of the periodic structure. In this approach, the structure is mathematically represented as a series of stacked slabs. The authors suggest that the structure must be divided into about 20 slabs to permit proper characterization of the structure. However, the authors note that performing an analysis with 40 variables (the width and height of 20 slabs) would be too computationally complex. Accordingly, the authors suggest reducing the complexity of the calculation by using sub-profiles and scaling factors. While such an approach achieves the goal of reducing computational complexity, it does so at the expense of limiting the accuracy of the analysis. Accordingly, it would be desirable to come up with an approach that was both highly accurate and could be performed on a real time basis.

BRIEF SUMMARY

To address this need, a system has been developed which permits the accurate evaluation of the characteristics of a periodic structure on a real time basis. In a first aspect of the subject invention, an improved analytical approach has been developed for increasing the efficiency of the calculations while maintaining a high degree of accuracy. In this aspect of the invention, a theoretical model of the structure is created. This initial model preferably has a single height and width defining a rectangular shape. Using Maxwell's equations, the model's response to the interaction with the probing radiation is calculated. The calculated response is compared with the measured result. Based on the comparison, the model parameters are iteratively modified to generate a rectangle which would produce calculated data which most closely matches to the measured data.

Using this information, a new model is created with more than one width and more than one layer. Preferably, a trapezoid is created with three layers. The model parameters are then adjusted using a fitting algorithm to find the trapezoidal shape which would produce the theoretical data closest to the measured data.

Using the results of this fitting process, the model is again changed, increasing the number of widths and layers. The fitting process is repeated. The steps of adding widths and layers and fitting the model to the data are repeated until the level of fitness of the model reaches a predetermined level.

During these iterative steps, the thickness of the layers (density of the layers) is permitted to vary in a manner so that a higher density of layers will be placed in regions where the change in width is the greatest. In this way, the curvature of the side walls can be most accurately modeled.

In this approach, the number of widths and layers is not fixed. It might be possible to fully characterize a structure with only a few widths and layers. In practice, this method has been used to characterize relatively complex structures with an average of 7 to 9 widths and 13 to 17 layers.

The scatterometry calculations associated with the early iterations of the models (square, trapezoid) are relatively simple and fast. However, as the number of widths and layers increase, the calculations become exponentially more difficult.

In order to be able to complete these calculations on a reasonable time scale, it was also necessary to develop a computing approach which minimized computational time. In another aspect of the subject invention, the scatterometry calculations are distributed among a group of parallel processors. In the preferred embodiment, the processor configuration includes a master processor and a plurality of slave processors. The master processor handles the control and the comparison functions. The calculation of the response of the theoretical sample to the interaction with the optical probe radiation is distributed by the master processor to itself and the slave processors.

For example, where the data is taken as a function of wavelength, the calculations are distributed as a function of wavelength. Thus, a first slave processor will use Maxwell's equations to determine the expected intensity of light at selected ones of the measured wavelengths scattered from a given theoretical model. The other slave processors will carry out the same calculations at different wavelengths. Assuming there are five processors (one master and four slaves) and fifty wavelengths, each processor will perform ten such calculations for each iteration.

Once the calculations are complete, the master processor performs the best fit comparison between each of the calculated intensities and the measured normalized intensities. Based on this fit, the master processor will modify the parameters of the model as discussed above (changing the widths or layer thickness). The master processor will then distribute the calculations for the modified model to the slave processors. This sequence is repeated until a good fit is achieved.

This distributed processing approach can also be used with multiple angle of incidence information. In this situation, the calculations at each of the different angles of incidence can be distributed to the slave processor.

Further objects and advantages will become apparent with the following detailed description taken in conjunction with the drawings in which:

DETAILED DESCRIPTION

Figure 1:
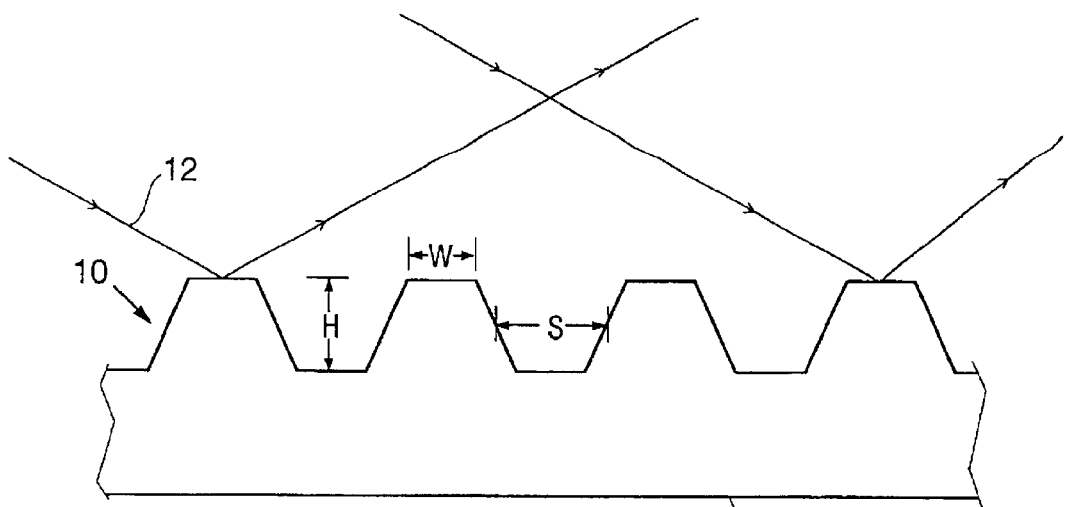
FIG. 1 is schematic diagram of a periodic surface feature known in the prior art.
Figure 2:
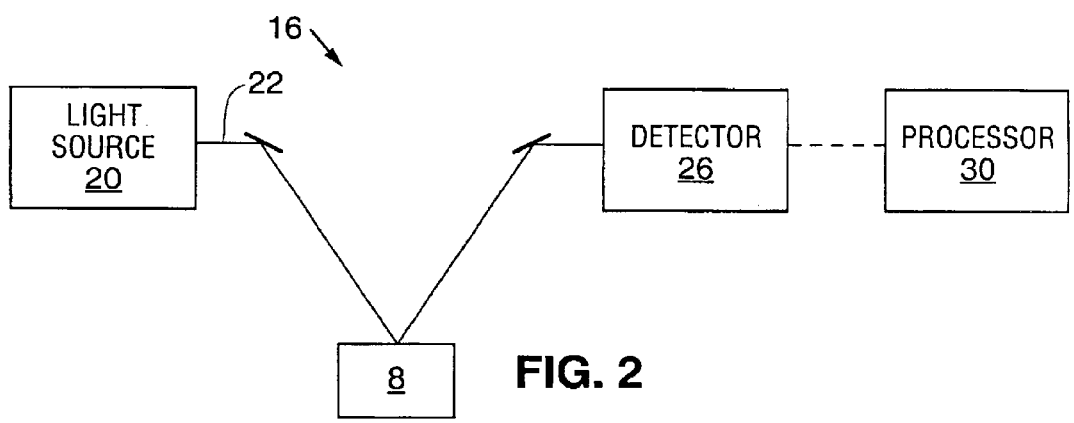
FIG. 2 is a block diagram of a system for performing the methods of the subject invention.

FIG. 2 is a block diagram of a system 16 for performing scatterometry measurements on a sample 8 having a periodic structure. For the purposes of this disclosure, the periodic structure means any repeating feature, where the feature size is about the same or smaller than the beam of light probing the sample such that at least some of the light is scattered rather than specularly reflected.

The system 16 includes a light source 20. As noted above, scatterometry measurements are often made using a broad band light source generating a probe beam 22 having a plurality of wavelengths. As described in U.S. patent application Ser. No. 09/818,703 cited above, the light can also be from a laser. In such a case, measurements would be taken as a function of angle of incidence, preferably without moving the sample.

Probe beam is directed to the sample. Typically a lens (not shown) is used to focus the probe beam to a small spot on the sample. The reflected probe beam is captured and measured by detector 26. The measured intensity of the probe beam will be affected by the amount of light scattered by the periodic structure. More specifically, the proportion of light diffracted into higher orders varies as a function of wavelength and angle of incidence such that the amount of light redirected out of the path to the detector also varies thereby permitting the scattering effects to be observed.

The configuration of the detector will be based on the type of measurement being made. For example, a single photodetector can be used to measure spectroscopic reflected intensity as long as a tunable wavelength selective filter (monochrometer) is located in the path of the probe beam. Given the desire to minimize measurement time, a spectrometer is typically used which includes a wavelength dispersive element (grating or prism) and an array detector to measure multiple wavelengths simultaneously. An array detector can also be used to measure multiple angles of incidence simultaneously. If spectroscopic ellipsometry measurements are to be made, the detection system will include some combination of polarizers, analyzers and compensators.

The various measurement modalities discussed above are well known in the art and will not be discussed herein. It should be noted that commercial devices are available that can make multiple measurements. Examples of such devices are described in U.S. Pat. No. 5,608,526 and PCT Application WO 99/02970, both of which are incorporated herein by reference.

The signals generated by the detector are supplied to a processor 30. The processor 30 need not be physically located near the detector. It is only required that the measurements from the detector be supplied to the processor. Preferably, there is an electrical connection between the detector and the processor, either directly or through a network. As is well known to those skilled in the art, the processor will also be supplied with other signals from the system 10 to permit normalization of the signals. For example, a detector (not shown) would be provided,to measure the output power of the light source so that variations in the output power of the light source could be taken into account during the calculations.

Figure 3:
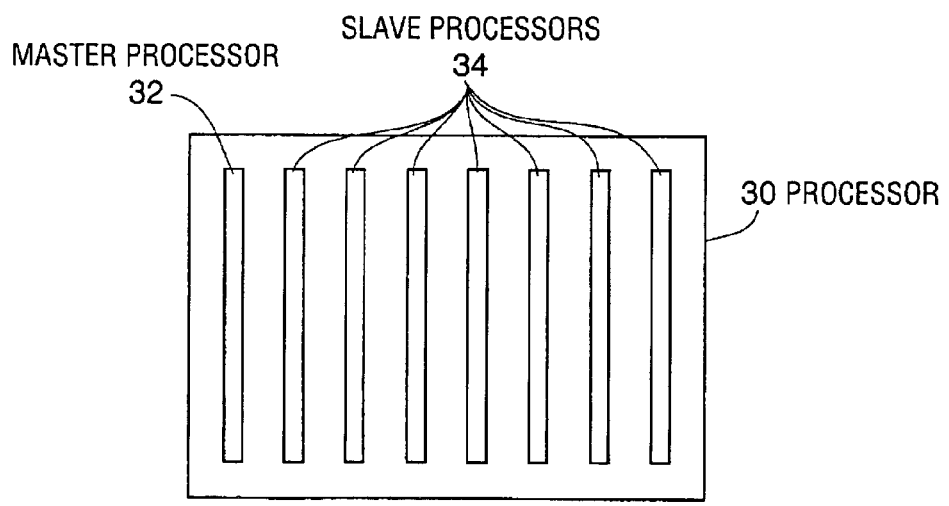
FIG. 3 is a simplified schematic of the processor used for performing the methods of the subject invention.

In the preferred embodiment, and as shown in FIG. 3, the architecture of the processor 30 consists of a plurality of microprocessor units linked by an Ethernet connection. The operating software is arranged to set one of the processors as a master 32 and the remainder of the processors as slaves 34. The master handles the higher level functions and distributes the tasks and retrieves the results from the slaves. Such a system is available commercially from Linux Networkx, Inc., under the trade name Evolcity. In the system used to evaluate the subject invention, an eight processor configuration was selected with each processor operating at 1.3 gigahertz. When properly combined, the system will operate at a speed equivalent to about 10 gigahertz. The approach for distributing the processing tasks will be discussed below.

As noted above, a wide variety of methods have been developed for evaluating characteristics of a periodic structure based on measured data. The approach described herein falls within the general class of procedures where an initial model is created and calculations are performed to determine the expected response of that sample to interaction with light. The model is then iteratively modified until the results of the calculation are close to the actual measured (and normalized) data. The subject approach can be contrasted with the earlier approaches which required the fabrication of many references samples, each of which would be measured, with the results stored for later comparison to the test sample. This subject approach is also different from the library approach where large numbers of configurations and their associated optical responses are created and stored for later comparison.

The subject approach recognizes that the shape of the structure can be represented as a plurality of stacked layers. However, rather than evaluate the sample based on a preordained, fixed number of layers, the algorithm is designed to progressively add layers, while seeking a best fit at each model level. This progression allows a theoretical structure which is relatively close the actual structure to be efficiently determined. In this approach, only the minimum number of layers which is actually necessary to achieve the desired level of fitness must be analyzed.

Figure 5:
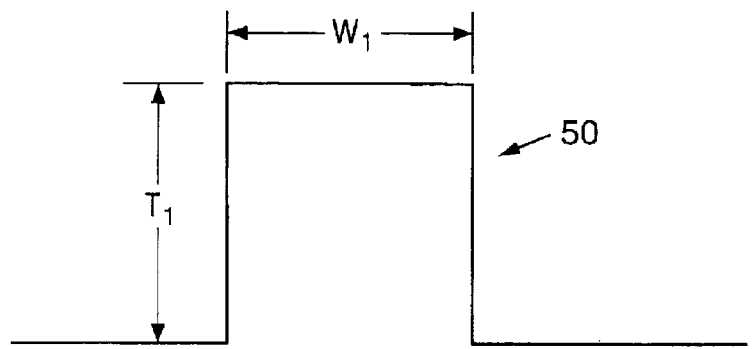
FIG. 5 illustrates the shape of the model in a first step of the subject method.
Figure 6:
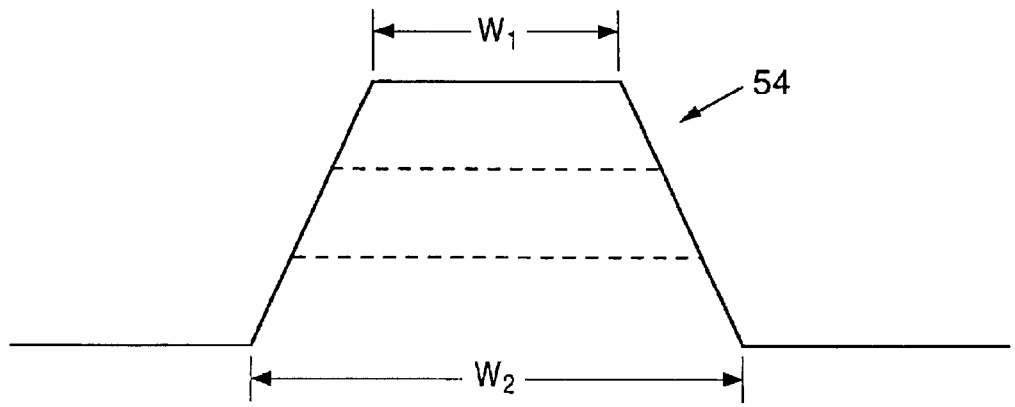
FIG. 6 illustrates the shape of the model in a subsequent step of the subject method.

The subject method will be described with respect to the flow chart of FIG. 4 and the drawings of FIGS. 5 to 7.

In the initial step 102, a rectangular model 50 (FIG. 5) is created. Typically, the model is created using seed values based on the expected characteristics of the sample. For example, the model will include information such as the index of refraction and extinction coefficient of the material. It is possible that this information can be obtained by measuring a region of the wafer which is not patterned. The model will also have a value for the height $H_1$ and width $W_1$.

The processor will then calculate the expected intensity that would be measured from a sample having a periodic structure with these initial characteristics (step 104). For the purposes of this example, it will be assumed that the measured data is obtained from a spectroscopic reflectometer. Accordingly, for each of the measured wavelengths, the processor will determine, using Maxwell's equations and a rigorous coupled wave theory, the expected normalized measured intensity of light reflected from the theoretical model. In a typical example, a measurement might include 50 to 100 wavelengths.

Once this calculation has been performed for each of the wavelengths, the results are compared to the normalized measurements obtained from the sample (step 106). This comparison can be done with a conventional least squares fitting algorithm, for example Levenberg-Marquardt. The result of this comparison will be used to modify the parameters of the model, in this case the starting height and width (step 108). The processor then calculates the expected intensity of reflected light at each wavelength from a structure with the modified attributes (step 110). These new values are compared to measured values and, if necessary, the model is once again modified. In practice, the iterative process usually needs to be repeated some 4 to 8 times before a suitable fit is achieved. The operator can define the desired level of fitness, i.e., when the differences between the model and the actual measurements as represented by the result of the comparison drops below a predetermined value. The best fit result will be a rectangle which most closely approximates the actual periodic structure.

The next step is to modify the model by increasing its complexity (step 114). More specifically, the shape or grating profile is changed from a simple rectangle to a trapezoid (see 54 in FIG. 6) having a top width $W_1$ and an independent bottom width $W_2$. In addition, the structure will be divided in a plurality of rectangular layers, in this case preferably three. Rather than using a polynomial expansion, the modification of this model is done using spline coefficients. The starting point for the modification is the best fit rectangle determined in the previous step.

The grating profile is defined using a class of spline algorithms including the well known cubic spline, Bezier-curves, B-spline and its more generalized form of non-uniform rational B-splines (The NURBS Book, by Les Piegl and Wayne Tiller, Springer, 1995). The benefits of such an approach are that 1) the curves are controlled by a set of control points and 2) the shape described by splines is more flexible than that described by polynomial expansions. A B-spline curve is described as $$C(u) = \operatorname{sum}_j N_j(u) P_j$$

where $P_j$ are the control points which can be scalars or vectors depending the desired flexibility. To minimize the number of fitting parameters for cubic splines, a user has the flexibility to choose different ways to allocate the spline points, in the vertical direction. Assuming that the grating height is scaled between 0 and 1 and assuming that the points $t_j$ are evenly distributed between 0 and 1, we then use a sigmoid function of the following form to transform $t_j$ to $u_j$: as (David Elliot, J. Australian Math. Soc. B40(E), pE77–E137, 1998):

$$u = f''(t)/(f''(t) + f''(1-t))\ f(t) = t(1 + c(1-t)),$$

where $c = 2(n/l - 1)$ and $n > \max(1, \tfrac{1}{2})$.

The effect of this transformation is that the spline points are more densely allocated at the two ends when $n \geq 1$. This is very close to how the nodes are distributed in Gaussian integration. It also corresponds to the more common periodic profiles which have more curvature near the top and bottom of the structure.

Another aspect of our algorithm involves how the system is divided into slices or layers (discretized). The simplest approach is to divide the grating evenly in each material. However, similar to how spline points are allocated, we can also discretize the system similar to the Gaussian integration which is again similar to the Sigmoid function described earlier. Significantly, we also use the idea of adaptively discretizing the system according to the curvature of the curve. In this approach, we allow the assignment of layers to be actively varied, along with the other characteristics of the model, during the fitting process. In this process, we define $d = \int du |dw/du|$, then each segment (between spline points) should have $d/n$ slices, where $w$ is the width as a function of height $u$, and $n$ is the total number of slices in the model.

Once the starting parameters are defined, the processor will calculate the expected intensity for this new structure at each of the measured wavelengths (step 116). The results are compared to the measured values (step 118) and if the fit is not acceptable, the model is modified (120). In accordance with the subject method, the algorithm is free to modify the widths and layer thicknesses regardless of the values obtained in previous steps. The algorithm is also designed to adjust the layer thickness such that the greater number of layers will be used to define regions where the width is changing the fastest. This procedure is repeated until a trapezoid which most closely approximates the actual periodic structure is determined.

Figure 7:
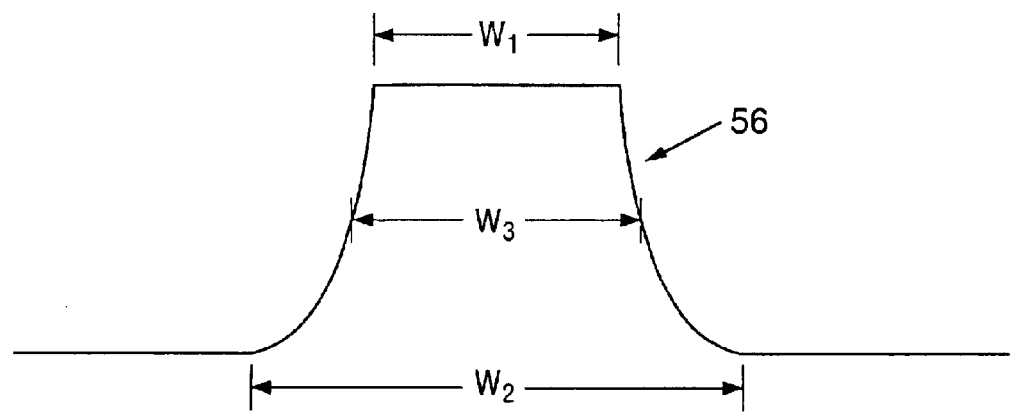
FIG. 7 illustrates the shape of the model in a subsequent step of the subject method.

Once the best fit trapezoid is defined, the complexity of the model is again increased to include one or more widths and layers (Step 130, and FIG. 7). In the preferred embodiment, the model is modified by adding a single extra width. The number of layers is also increased. Preferably, the number of layers at each iteration is at least 2Y−1 (where Y is the number of widths) but no greater than 2Y+1.

The processor will then calculate the expected intensity for this new structure at each of the measured wavelengths (step 134). The results are compared to the measured values (step 136) and if the fit is not acceptable, the model is modified (140). This procedure will repeat in an iterative fashion until the model with the selected number of widths and layers best fits the data. If that structure meets the overall predetermined level of fitness, the process is complete and the model will suitably match the actual periodic structure (step 142). If not, the processor will loop back (along path 144) to create a new model with additional widths and layers (See 56 in FIG. 7). In an initial experiments, the average number of widths and layers needed to adequately characterize a structure was about 7 to 9 widths and 13 to 17 layers. With these additional widths and layers, structures with various wall profiles can be analyzed.

As noted above, one feature of the subject method is its ability to permit the thickness and density of the theoretical layers to vary during each iteration. It should be noted, however, that some periodic structures under investigation will include actual physical layers. If so, these physical layers can be used as boundaries to further define or constrain the model.

The calculations required to determine the response of a sample to incident radiation are complex. As the number of widths and layers increases, the time required to make the calculations increases dramatically. Accordingly, in a second aspect of the subject invention, the processing tasks are distributed to a parallel processor system.

In the preferred embodiment, one of the eight processors (FIG. 3) is configured as the master processor 32 and the remaining seven processors are slaves 34. The master processor controls the overall analysis and distributes certain of the functions to the slave processors. As noted above, the most time consuming portion of the calculation is the determination of the optical response of the model to a each of the different measured wavelengths or angles of incidence. The comparison of these theoretical results with the measured signals and the modification of the model can, by comparison, be handled relatively quickly.

Figure 4:
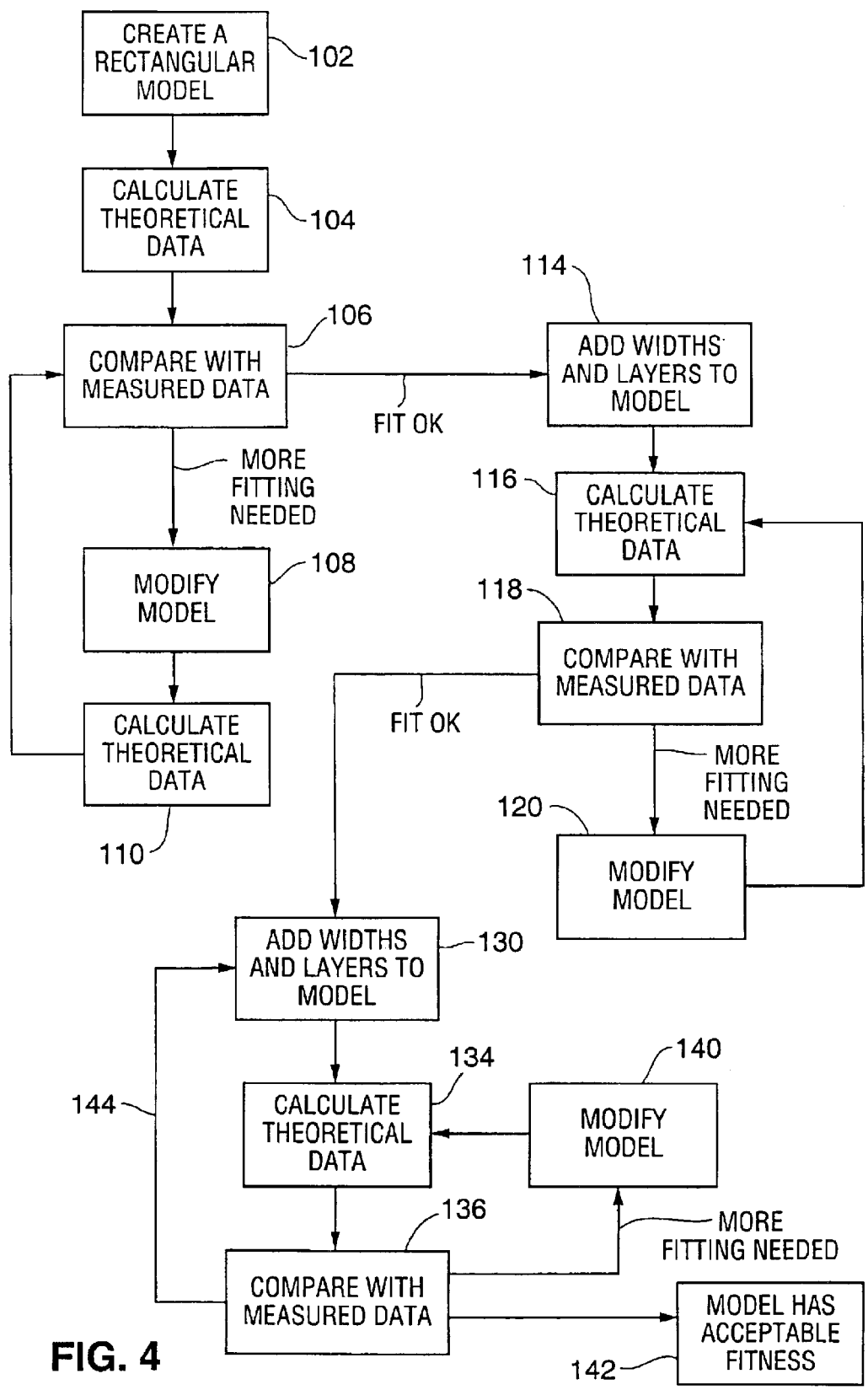
FIG. 4 is a flow chart illustrating the subject approach for analyzing optical data to evaluate characteristics of a periodic structure.

Therefore, in the preferred embodiment of the subject invention, the master processor is responsible for distributing the calculations of theoretical data to the slave processors (such calculations being shown as steps 104, 110, 116 and 134 in FIG. 4). In the preferred embodiment, the master processor would also participate in these calculations.

A maximum reduction in computational time can be achieved if the workload is evenly distributed. The preferred approach to achieve uniformity is to distribute the wavelength or angle of incidence information serially across the processors. Thus, the first slave processor (in an eight processor system) would be responsible for calculating the first (shortest) wavelength as well as the ninth, seventeenth, etc. (n+8). The second slave processor would be responsible for the second (next shortest) wavelength as well as the tenth, eighteenth, etc. This approach can be used for both spectrophotometry and spectroscopic ellipsometry. A similar approach can be used with multiple angle of incidence measurements wherein the first, eighth, seventeenth measured angle would be calculated by the first slave processor, etc.

Once each of the calculations is made at each of the wavelengths (or angles), the master processor will compare the results at each of the wavelengths to the normalized measurements at the corresponding wavelengths. The difference will define the level of fitness of the result and will be used to determine if another iteration is required. The calculations necessary for each iteration of the model are again distributed to the slave processors in the manner discussed above.

While the subject invention has been described with reference to a preferred embodiment, various changes and modifications could be made therein, by one skilled in the art, without varying from the scope and spirit of the subject invention as defined by the appended claims. For example, it should be apparent that the inventions described herein are not specifically dependent upon the particular scatterometry approach used to collect the data. Data can be obtained from spectroscopic reflectometers or spectroscopic ellipsometers. It should be noted that spectroscopic reflectometers can obtain data from probe beams directed either at normal incidence or off-axis to the sample. Similarly, spectroscopic ellipsometers can obtain data from probe beams directed either at normal incidence or off-axis to the sample. Data can also be obtained from multiple angle of incidence devices. As noted in U.S. patent application Ser. No. 09/818,703, applicant has developed a variety of simultaneous multiple angle of incidence devices that would be suitable. Detailed descriptions of assignee's simultaneous multiple angle of incidence devices can be found in the following U.S. Pat. Nos. 4,999,014; 5,042,951; 5,181,080; 5,412,473 and 5,596,411, all incorporated herein by reference. It should also be understood, that data from two or more of the devices can be combined to reduce ambiguities in the analysis. Such additional data can be combined in the regression analysis discussed above.

See also, U.S. Pat. No. 5,889,593 incorporated by reference. In this patent, a proposal is made to include an optical imaging array for breaking up the coherent light bundles to create a larger spot to cover more of the periodic structure.

We claim:

1. An apparatus for analyzing the characteristics of a periodic structure formed on a sample, comprising:
    a spectroscopic measurement system including a broad band probe beam directed to reflect off the periodic structure and a detection module for measuring one of a change in magnitude and a phase of the broad band probe beam at a plurality of wavelengths and generating output signals corresponding thereto; and
    a processor system using the output signals generated by the spectroscopic measurement system to determine a rectangular model with a theoretical height and width for an element of the periodic structure which provides the best fit with the measurements made by the spectroscopic measurement system, the processor system deriving a second model using the determined rectangular model, the second model having a top width different from a bottom width and including at least two layers, the processor system capable of iteratively modifying a height and width of each of the at least two layers to determine the best fit with the measurements made by the spectroscopic measurement system and adding additional theoretical intermediate widths and layers to the second model in an iterative best fit process until the level of fitness reaches a predetermined level.

2. An apparatus as recited in claim 1, wherein:
    said spectroscopic measurement system is one of a spectroscopic reflectometer and a spectroscopic ellipsometer.

3. An apparatus as recited in claim 1, wherein:
    the second model is formulated using spline algorithms.

4. An apparatus as recited in claim 1, wherein: the second model is formulated with cubic splines.

5. An apparatus for analyzing the characteristics of a periodic structure formed on a sample, comprising:
    a spectroscopic measurement system including a broad band probe beam directed to reflect off the periodic structure and a detection module for measuring either the change in magnitude or phase of the broad band probe beam at a plurality of wavelengths and generating output signals corresponding thereto; and
    a processor system for evaluating the characteristics of the periodic structure based on the output signals, said processor system for defining a first theoretical model with no more than two different widths and at least one layer and modifying that first theoretical model to find a best fit with the measurements made by the spectroscopic measurement system for an element of the periodic structure, and for deriving subsequent models each having an increased number of theoretical layers and using a fitting algorithm to iteratively adjust a height and width of each of the theoretical layers until one of the subsequent theoretical models defines a structure which approximates the configuration of the periodic structure to a predetermined fitness level.

6. An apparatus as recited in claim 5, wherein:
    said spectroscopic measurement system is one of a spectroscopic reflectometer and a spectroscopic ellipsometer.

7. An apparatus as recited in claim 5, wherein:
    each subsequent model is formulated using a spine algorithm, wherein a number of slices between spline points is equal to d/n, where $d = \int du \, |dw/du|$, w is the width as a function of height u, and n is the total number of slices in each subsequent model.

8. An apparatus as recited in claim 5, wherein:
    the number of layers in each subsequent model is at least 2Y−1 but no greater than 2Y+1, where Y is the number of widths.

9. An apparatus as recited in claim 5, wherein:
    each layer in each subsequent model is rectangular in shape.

10. An apparatus as recited in claim 5, wherein:
    the sample including the periodic structure includes more than one physical layer, wherein during modification of a subsequent model the theoretical layers are constrained by the physical layer structure of the sample.

* * * * *